(12) United States Patent
Yamashita et al.

(10) Patent No.: US 10,772,490 B2
(45) Date of Patent: Sep. 15, 2020

(54) MONITORING DEVICE AND METHOD OF OPERATING THE SAME

(71) Applicant: HAMAMATSU PHOTONICS K.K., Hamamatsu-shi, Shizuoka (JP)

(72) Inventors: Daisuke Yamashita, Hamamatsu (JP); Yutaka Yamashita, Hamamatsu (JP); Yukio Ueda, Hamamatsu (JP); Yoshinori Tamaoki, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 85 days.

(21) Appl. No.: 15/714,048

(22) Filed: Sep. 25, 2017

(65) Prior Publication Data

US 2018/0084982 A1  Mar. 29, 2018

(30) Foreign Application Priority Data

Sep. 27, 2016 (JP) ................. 2016-188257

(51) Int. Cl.
   *A61B 1/07* (2006.01)
   *A61M 25/00* (2006.01)
   (Continued)

(52) U.S. Cl.
   CPC .............. *A61B 1/07* (2013.01); *A61B 5/0084* (2013.01); *A61B 5/0261* (2013.01); *A61B 18/245* (2013.01); *A61M 25/0043* (2013.01); *G02B 6/0001* (2013.01); *G02B 6/10* (2013.01); *G02B 6/241* (2013.01); *A61B 18/26* (2013.01); *A61B 2018/00785* (2013.01); *A61N 2005/0602* (2013.01)

(58) Field of Classification Search
   CPC ......... A61B 1/07; A61B 18/245; A61B 18/20; A61N 2005/0602
   See application file for complete search history.

(56) References Cited

U.S. PATENT DOCUMENTS

| | | | | |
|---|---|---|---|---|
| 4,691,709 A | * | 9/1987 | Cohen ................ | A61B 5/02154 600/480 |
| 4,718,406 A | * | 1/1988 | Bregman ............. | A61B 1/0005 600/113 |

(Continued)

FOREIGN PATENT DOCUMENTS

| | | |
|---|---|---|
| JP | S60-106444 A | 6/1985 |
| JP | 2000-508938 A | 7/2000 |

(Continued)

*Primary Examiner* — Mallika D Fairchild
*Assistant Examiner* — Sana Sahand
(74) *Attorney, Agent, or Firm* — Faegre Drinker Biddle & Reath LLP

(57) ABSTRACT

A device for radiating pulsed light toward a thrombus in a blood vessel includes a light source configured to output monitoring light to be radiated into the blood vessel, a light detector configured to detect returned light of the monitoring light and output a detection signal, and a computer configured to acquire a time waveform, which is a change in an intensity of the returned light over time, based on the detection signal, wherein the computer is configured to obtain a parameter on the basis of the time waveform and evaluates a reaction in the blood vessel according to the radiation of the pulsed light on the basis of the parameter.

16 Claims, 16 Drawing Sheets

(51) Int. Cl.
 *A61B 5/00* (2006.01)
 *A61B 5/026* (2006.01)
 *G02B 6/24* (2006.01)
 *A61B 18/24* (2006.01)
 *F21V 8/00* (2006.01)
 *G02B 6/10* (2006.01)
 *A61B 18/00* (2006.01)
 *A61N 5/06* (2006.01)
 *A61B 18/26* (2006.01)

(56) References Cited

U.S. PATENT DOCUMENTS

| | | | | |
|---|---|---|---|---|
| 5,944,687 | A * | 8/1999 | Benett | A61B 18/26 604/22 |
| 6,428,531 | B1 * | 8/2002 | Visuri | A61B 18/245 128/898 |
| 6,538,739 | B1 * | 3/2003 | Visuri | A61B 18/26 356/388 |
| 2002/0045811 | A1 * | 4/2002 | Kittrell | A61B 1/00096 600/407 |
| 2002/0045890 | A1 * | 4/2002 | Celliers | A61B 18/26 606/7 |
| 2009/0299354 | A1 * | 12/2009 | Melsky | A61B 18/245 606/16 |
| 2011/0077528 | A1 * | 3/2011 | Kemp | A61B 5/0066 600/476 |
| 2012/0065490 | A1 * | 3/2012 | Zharov | A61B 5/0059 600/407 |
| 2013/0046293 | A1 * | 2/2013 | Arai | A61B 18/24 606/15 |
| 2015/0133728 | A1 * | 5/2015 | Finkman | A61B 18/245 600/108 |

FOREIGN PATENT DOCUMENTS

| | | |
|---|---|---|
| JP | 2001-517805 A | 10/2001 |
| WO | WO-97/39690 A1 | 10/1997 |
| WO | WO 99/016366 | 4/1999 |

* cited by examiner

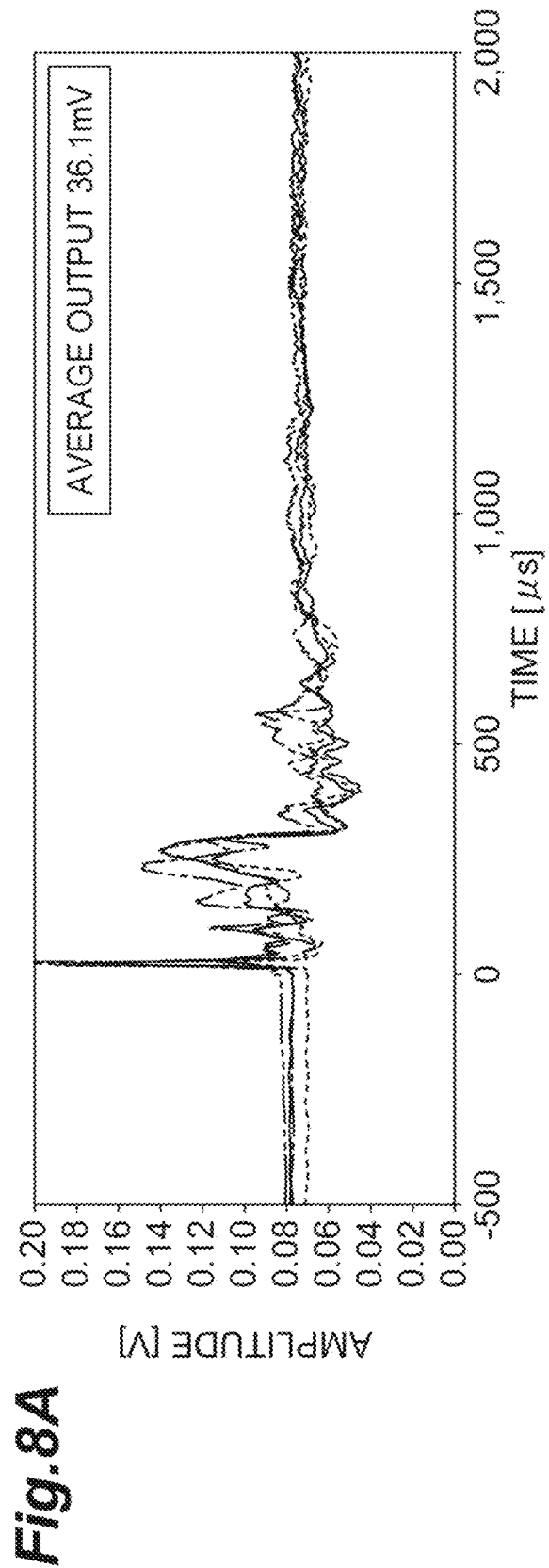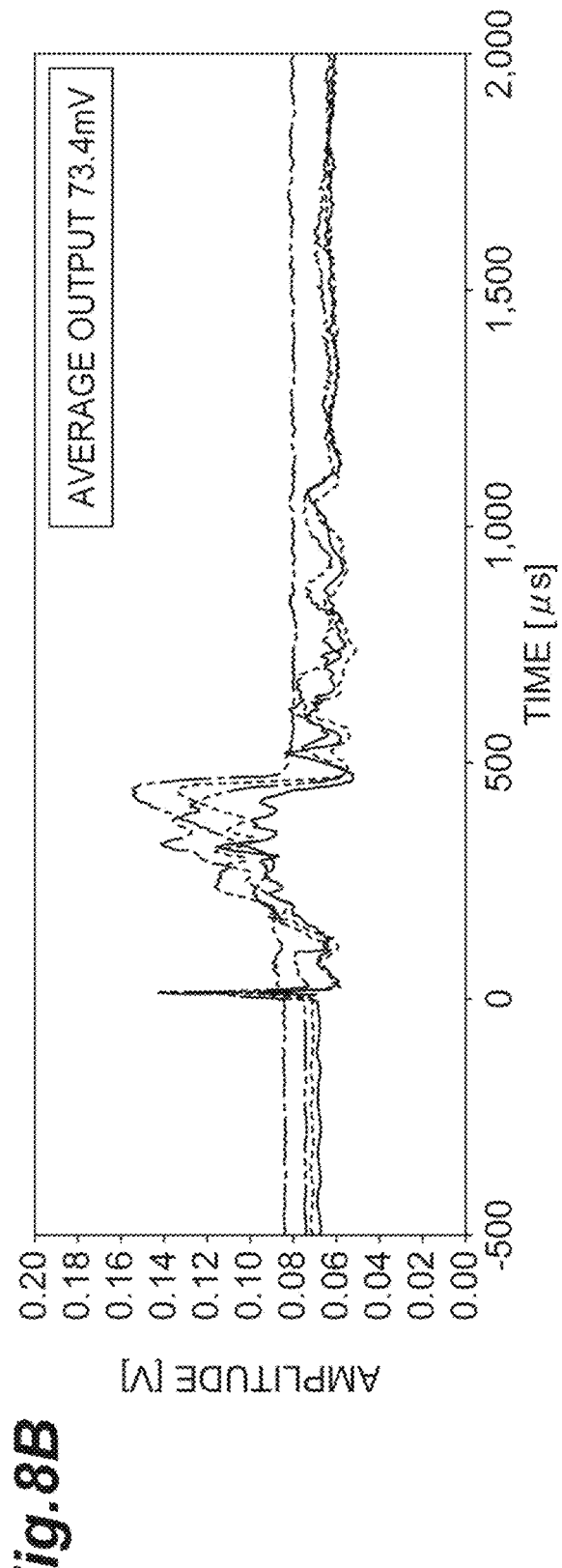
Fig. 8A
Fig. 8B

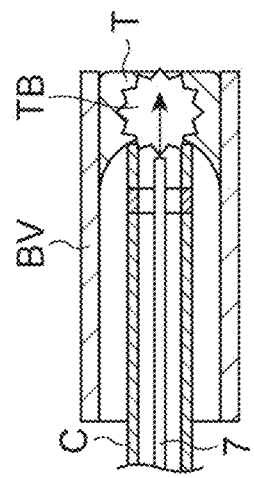 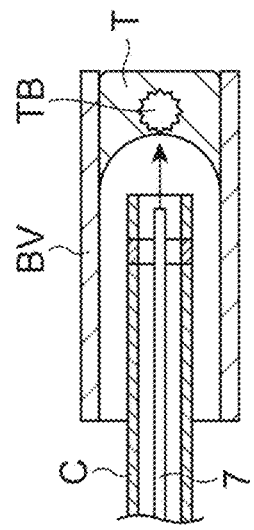
*Fig.11A*
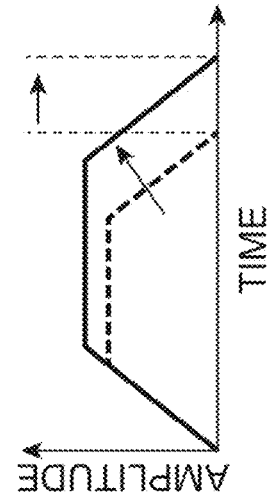 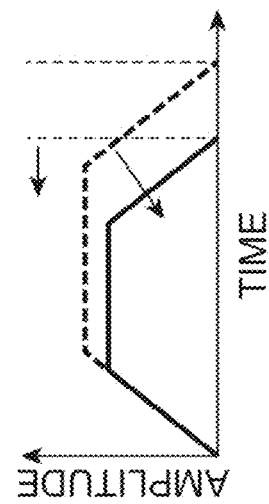
*Fig.11B*
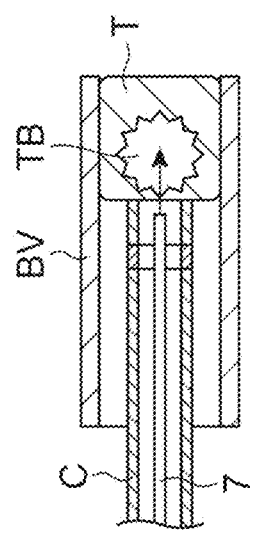 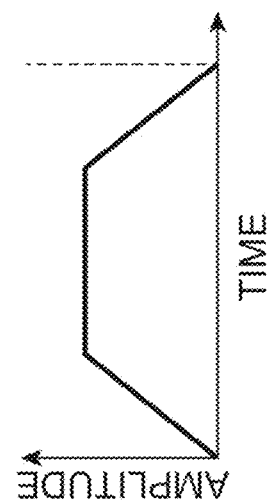
*Fig.11C*

MONITORING DEVICE AND METHOD OF OPERATING THE SAME

TECHNICAL FIELD

The technical field relates to a monitoring device and a method of operating the same.

BACKGROUND

Conventionally, an angioplasty device for removing a thrombus formed in a blood vessel is known. For example, an angioplasty device disclosed in Japanese Unexamined Patent Publication No. 2000-508938 includes a catheter including an optical fiber and a laser system connected to the optical fiber. In the angioplasty device, pulsed light is output from a distal end of the optical fiber, and a thrombus is dissolved by a bubble generated by the pulsed light. In such an angioplasty device, a positional relationship between the optical fiber and a thrombus is identified by injecting a contrast medium into a blood vessel to acquire an X-ray image.

SUMMARY

In one embodiment, a device for radiating pulsed light toward a thrombus in a blood vessel, the device including: a light output unit configured to output monitoring light to be radiated into the blood vessel; a light detection unit configured to detect returned light of the monitoring light and output a detection signal; and an analysis unit configured to acquire a time waveform, which is a change in an intensity of the returned light over time, on the basis of the detection signal, wherein the analysis unit obtains a parameter on the basis of the time waveform and evaluates a reaction in the blood vessel according to the radiation of the pulsed light on the basis of the parameter.

In one embodiment, a method for radiating pulsed light toward a thrombus in a blood vessel, the method including: a step of outputting monitoring light to be radiated into the blood vessel; a step of detecting returned light of the monitoring light by a light detection unit and outputting a detection signal; a step of acquiring a time waveform, which is a change in an intensity of the returned light over time, on the basis of the detection signal; a step of obtaining a parameter on the basis of the time waveform; and a step of evaluating a reaction in the blood vessel according to the radiation of the pulsed light on the basis of the parameter.

BRIEF DESCRIPTION OF THE DRAWINGS

FIG. 8A is a graph illustrating a time waveform measured by the monitoring device.

FIG. 8B is a graph illustrating a time waveform measured by the monitoring device.

FIG. 11A is a schematic diagram illustrating a relationship between a state in a blood vessel and the time waveform measured by the monitoring device.

FIG. 11B is a schematic diagram illustrating a relationship between the state in the blood vessel and the time waveform measured by the monitoring device.

FIG. 11C is a schematic diagram illustrating a relationship between the state in the blood vessel and the time waveform measured by the monitoring device.

DETAILED DESCRIPTION

Figure 1:
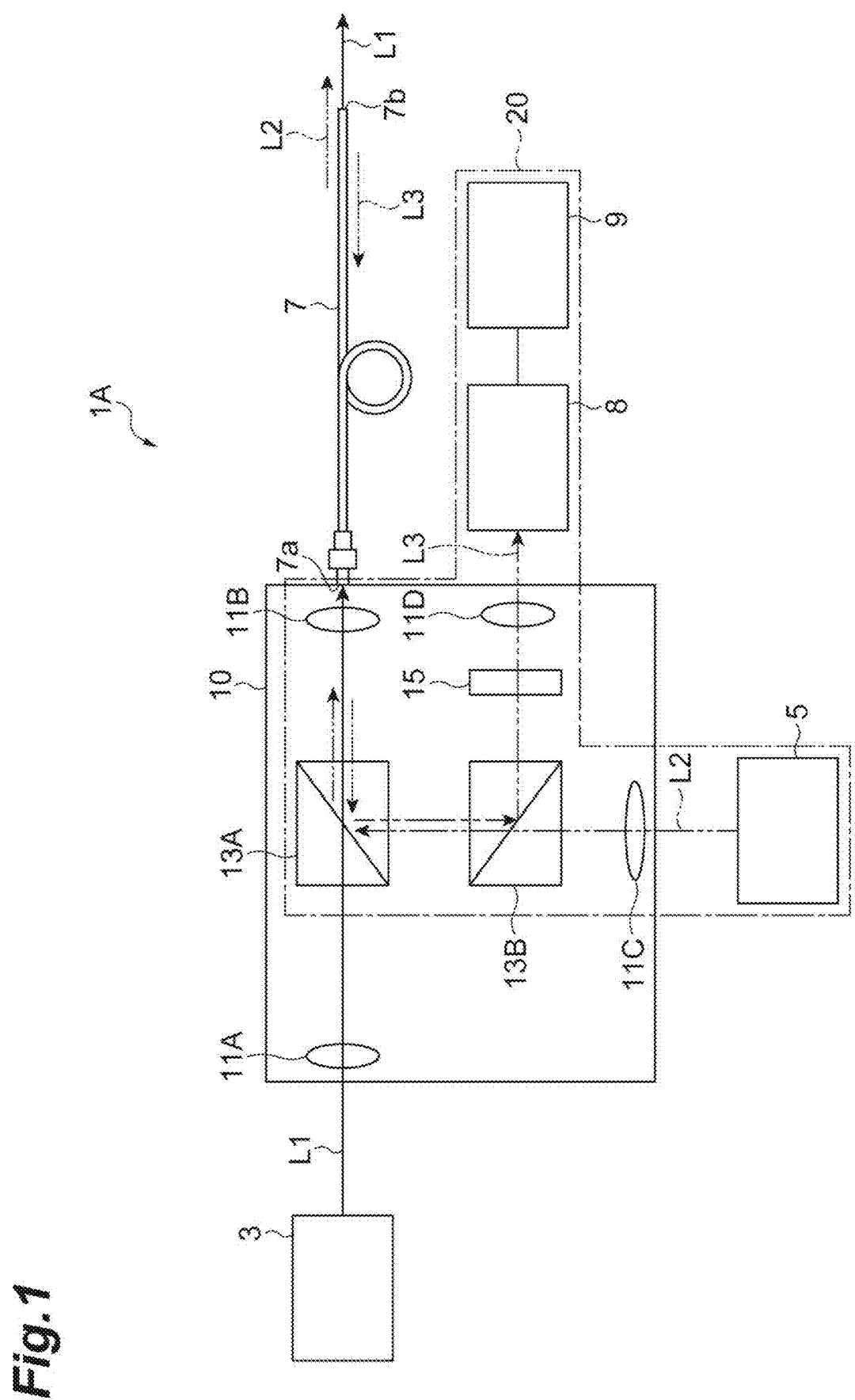
FIG. 1 is a schematic diagram illustrating a light radiation device to which a monitoring device according to an embodiment is applied.

Hereinafter, embodiments will be specifically described with reference to the drawings. For the sake of convenience, the substantially same elements are denoted by the same reference numerals, and descriptions thereof may be omitted.

First Embodiment

FIG. 1 is a schematic diagram illustrating a light radiation device 1A to which a monitoring device 20 according to the embodiment is applied. The light radiation device 1A illustrated in FIG. 1 is a device that radiates pulsed laser light L1 into a blood vessel. The light radiation device 1A is used for a therapy for, for example, an acute phase cerebral embolism and the like. The light radiation device 1A includes a therapeutic laser light source 3, a monitoring laser light source 5 (a light source or a light output unit), an optical fiber 7, a coupling optical system 10, a photodetector (a light detector or a light detection unit) 8, and an analysis unit 9.

In the present embodiment, the monitoring device 20 is constituted of some of the monitoring laser light source 5, the photodetector 8, the analysis unit 9, and the coupling optical system 10.

The therapeutic laser light source 3 outputs the pulsed laser light L1 used for removing a thrombus. The pulsed laser light L1 has a wavelength that can be absorbed by the thrombus and blood. For example, the pulsed laser light L1 is easily absorbed by the thrombus and blood if the wavelength of the pulsed laser light L1 is 500 to 600 nm. In the present embodiment, for example, the wavelength of the pulsed laser light L1 is about 550 nm, for example, 532 nm. A frequency of the pulsed laser light L1 is about 1 to 100 Hz, and a pulse width of the pulsed laser light L1 is about 50 μs to 200 μs. In the present embodiment, as an example, the frequency of the pulsed laser light L1 is 5 Hz, and the pulse width of the pulsed laser light L1 is 100 μs (see FIG. 3). An output of the therapeutic laser light source 3 can be, for example, 20 mW to 100 mW. For example, a laser diode or the like can be used as the therapeutic laser light source 3.

The monitoring laser light source 5 outputs monitoring light L2 radiated into the blood vessel. In the present embodiment, light having a wavelength that is unlikely to be absorbed by a thrombus and blood can be used as the monitoring light L2. For example, hemoglobin is liable to absorb light having a wavelength of less than 600 nm. Moisture easily absorbs light having a wavelength of 1000 nm or more. Thus, laser light having a wavelength of, for example, 600 nm to 1300 nm can be used as the monitoring light L2. Either continuous wave light or pulsed light may be used as the monitoring light L2. The monitoring light L2 in the present embodiment is continuous wave light (see FIG. 3). An output of the monitoring laser light source 5 is less than an output of the therapeutic laser light source 3. The output of the monitoring laser light source 5 may be, for example, 1 mW or more. For example, a laser diode or the like can be used as the monitoring laser light source 5.

The pulsed laser light L1 from the therapeutic laser light source 3 is input to one end surface 7a of the optical fiber 7. The optical fiber 7 guides the input pulsed laser light L1 and outputs the pulsed laser light L1 from the other end surface 7b thereof. The monitoring light L2 from the monitoring laser light source 5 is input to the one end surface 7a of the optical fiber 7. The optical fiber 7 guides the input monitoring light L2 and outputs the monitoring light L2 from the other end surface 7b thereof. The pulsed laser light L1 and returned light L3 of the monitoring light L2 are input to the other end surface 7b of the optical fiber 7. The optical fiber 7 guides the input returned light L3 and outputs the input returned light L3 from the one end surface 7a. The other end side of the optical fiber 7 is accommodated in a catheter C (see FIG. 10A and the like) to be inserted into a blood vessel. For example, the catheter C may be inserted into a narrow blood vessel having a diameter of 1 mm or less. Therefore, the catheter C has a diameter of 0.8 mm or less as an example. For example, a multimode optical fiber having a diameter of about 140 μm and a core diameter of about 100 μm may be used as the optical fiber 7. One end side of the optical fiber 7 is detachably connected to the coupling optical system 10. The optical fiber 7 and the catheter C accommodating the optical fiber 7 can be replaced, for example, every time therapy is performed.

The coupling optical system 10 optically connects the therapeutic laser light source 3 and one end of the optical fiber 7. The coupling optical system 10 inputs the pulsed laser light L1 output from the therapeutic laser light source 3 to the one end surface 7a of the optical fiber 7. The coupling optical system 10 optically connects the monitoring laser light source 5 and the one end of the optical fiber 7. The coupling optical system 10 inputs the monitoring light L2 output from the monitoring laser light source 5 to the one end surface 7a of the optical fiber 7. The coupling optical system 10 optically connects the one end of the optical fiber 7 and the photodetector 8. The coupling optical system 10 inputs the returned light L3 output from the one end surface 7a of the optical fiber 7 to the photodetector 8. The coupling optical system 10 includes four lenses 11A to 11D, two beam splitters 13A and 13B, and a band-pass filter 15. In the present embodiment, the lenses 11B, 11C, and 11D, the beam splitters 13A and 13B, and the band-pass filter 15 belong to the monitoring device 20.

The lenses 11A and 11B are disposed between the therapeutic laser light source 3 and the one end surface 7a of the optical fiber 7 on an optical path of the pulsed laser light L1 output from the therapeutic laser light source 3. The beam splitter 13A is disposed between the lens 11A and the lens 11B on the optical path of the pulsed laser light L1 output from the therapeutic laser light source 3. The monitoring light L2 output from the monitoring laser light source 5 is input to the beam splitter 13A. The beam splitter 13A is constituted of, for example, a half mirror or a dichroic mirror.

The beam splitter 13B is provided on an optical path of the monitoring light L2 output from the monitoring laser light source 5 and disposed between the monitoring laser light source 5 and the beam splitter 13A. The beam splitter 13B is constituted of, for example, a half mirror. The lens 11C is provided on the optical path of the monitoring light L2 output from the monitoring laser light source 5 and disposed between the monitoring laser light source 5 and the beam splitter 13B.

The band-pass filter 15 is provided on an optical path of the returned light L3 output from the beam splitter 13B and disposed between the beam splitter 13B and the photodetector 8. The band-pass filter 15 selectively passes a wavelength component of the monitoring light L2 in the returned light 13. The lens 11D is disposed between the band-pass filter 15 and the photodetector 8 on the optical path of the returned light L3 output from the beam splitter 13B.

The pulsed laser light L1 output from the therapeutic laser light source 3 becomes parallel light via the lens 11A, passes through the beam splitter 13A, and is input to the one end surface 7a of the optical fiber 7 via the lens 11B. The pulsed laser light L1 input to the one end surface 7a of the optical fiber 7 is output from the other end surface 7b of the optical fiber 7.

The monitoring light L2 output from the monitoring laser light source 5 becomes parallel light via the lens 11C, passes through the beam splitter 13B, and is input to the beam splitter 13A. The beam splitter 13A outputs the input monitoring light L2 to the lens 11B. Positions of the lens 11C and the beam splitter 13A are adjusted so that an optical axis of the monitoring light L2 output from the beam splitter 13A coincides with an optical axis of the pulsed laser light L1. The monitoring light L2 input to the lens 11B is input to the one end surface 7a of the optical fiber 7. The monitoring light L2 input to the one end surface 7a of the optical fiber 7 is output from the other end surface 7b of the optical fiber 7.

The returned light L3 from the optical fiber 7 becomes parallel light via the lens 11B and is input to the beam splitter 13A. The beam splitter 13A outputs the input returned light L3 to the beam splitter 13B. The beam splitter 13B outputs the returned light L3 to the band-pass filter 15. The returned light L3, which has the same wavelength component as the monitoring light L2 that passed through the band-pass filter 15, is input to the photodetector 8 through the lens 11D.

The photodetector 8 detects an intensity of the input returned light L3. Various elements such as a photomultiplier tube (PMT), an avalanche photodiode, a PIN photodiode, and a multi-pixel photon counter (MPPC) are used as the photodetector 8. The photodetector 8 is electrically connected to the analysis unit 9. The photodetector 8 photoelectrically converts the detected returned light L3 and outputs a signal (detection signal) indicating the intensity of the returned light L3 to the analysis unit 9.

On the basis of the returned light L3 detected by the photodetector 8, the analysis unit 9 evaluates a reaction in the blood vessel caused by the radiation of the pulsed laser light L1. On the basis of the signal indicating the intensity of the returned light L3 input from the photodetector 8, the analysis unit 9 of the present embodiment acquires a time waveform, which is a change in the intensity of the returned light L3 over time (hereinafter simply referred to as a "time waveform"). For example, the analysis unit 9 may acquire the time waveform in correspondence with each pulse of the pulsed laser light L1. The analysis unit 9 obtains a parameter on the basis of the acquired time waveform, and evaluates the reaction in the blood vessel according to the radiation of the pulsed laser light L1 on the basis of the parameter. At least one of a convergence time in the time waveform, a peak time in the time waveform, a peak intensity in the time waveform, a waveform pattern in the time waveform, the presence or absence of a peak in the time waveform, and an integrated value (a waveform area) of the time waveform is used as such a parameter. For example, an operator is notified of the evaluation result obtained by the analysis unit 9 as any output such as an image or sound.

The analysis unit 9 can be constituted of a computer including, for example, an AD converter for converting a signal output from the photodetector 8 into digital data, an arithmetic circuit such as a CPU in which arithmetic processing is performed, a storage device constituted of memories such as a RAM and a ROM, and an input/output device. For example, the analysis unit 9 may be constituted of a computer such as a personal computer, a microcomputer and/or a smart device (such as a smart phone or a tablet terminal). Also, the analysis unit 9 may be constituted of a computer such as a cloud server. In this case, the function of the analysis unit 9 may be implemented by the cloud server.

Next, a principle of measurement by the monitoring device 20 will be described.

Figure 2:
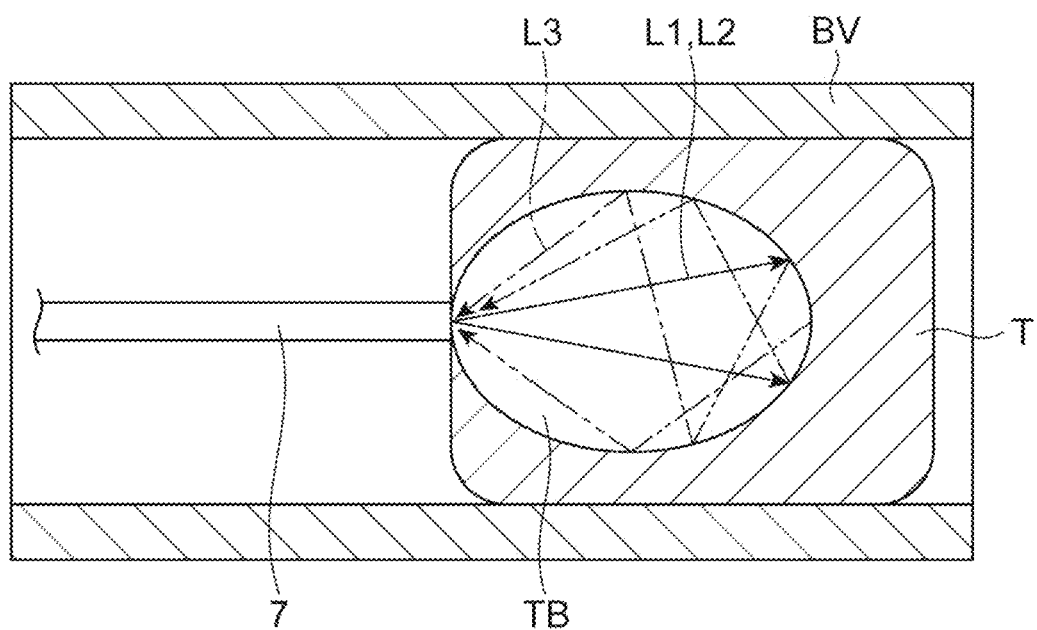
FIG. 2 is a schematic diagram illustrating a principle of measurement by the monitoring device.
Figure 3:
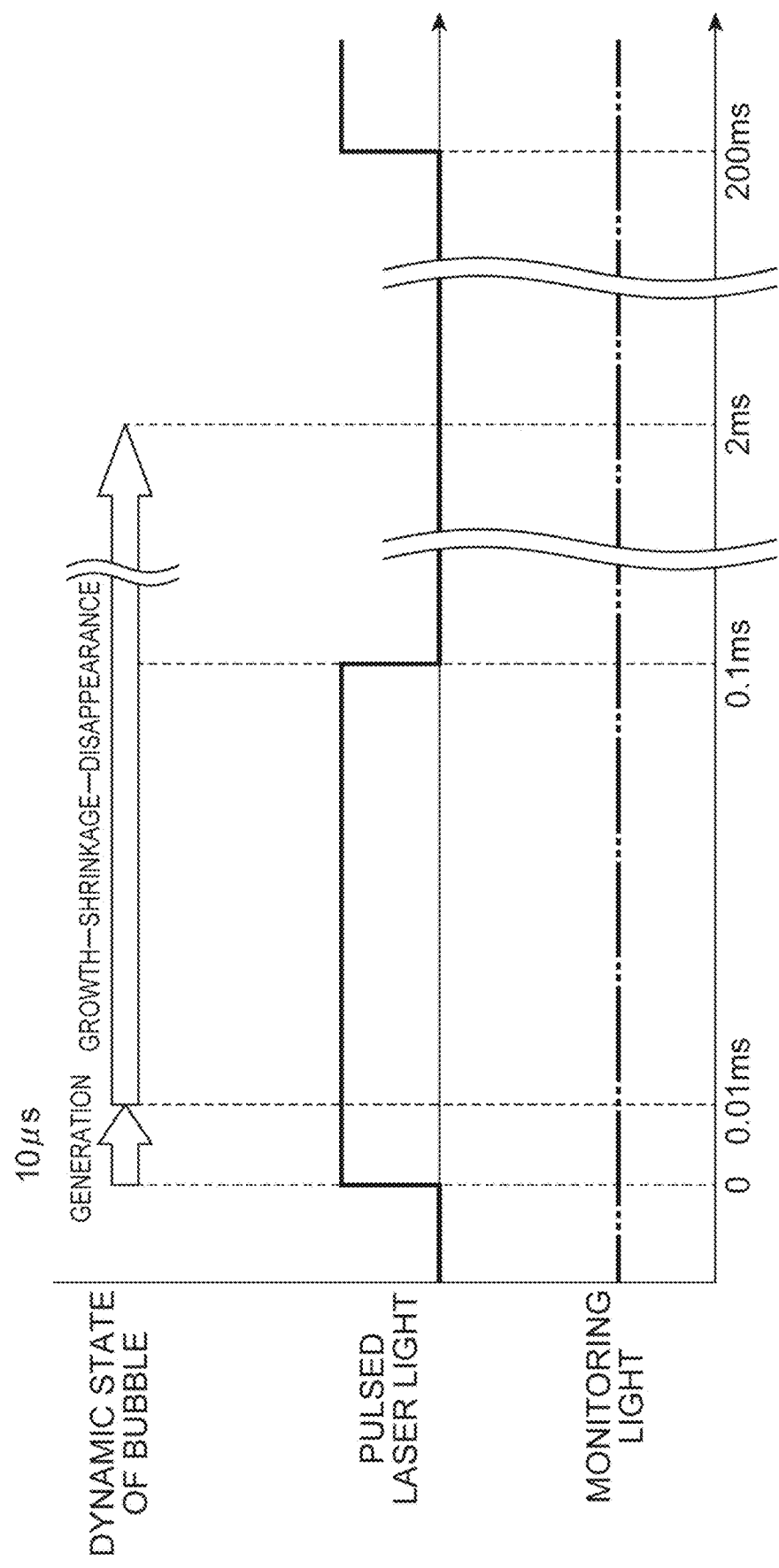
FIG. 3 is a diagram illustrating the principle of measurement by the monitoring device.

FIGS. 2 and 3 are diagrams illustrating the principle of measurement by the monitoring device 20. FIG. 2 schematically illustrates a reaction when the pulsed laser light L1 is radiated from the other end of the optical fiber 7 with respect to a thrombus T which inhibits a blood flow in a blood vessel BV. When the thrombus T is irradiated with the pulsed laser light L1, energy of the pulsed laser light L1 is selectively absorbed by the thrombus T. As a result, as illustrated in FIG. 2, a bubble TB is generated due to thermal action. The thrombus T in the blood vessel BV is cut or removed by a physical action of the bubble 1B.

When the bubble TB is generated in the blood vessel BV, the pulsed laser light L1 and the monitoring light L2 radiated from the optical fiber 7 are reflected or scattered by the bubble TB. At least a part of the reflected or scattered pulsed laser light L1 and monitoring light L2 is input to the other end of the optical fiber 7 and becomes the returned light L3. In the present embodiment, the returned light L3 passes through the band-pass filter 15 so that the wavelength component of the monitoring light L2 in the returned light L3 is mainly input to the photodetector 8.

FIG. 3 illustrates an example of a timing chart of a dynamic state of the bubble TB generated by the radiated pulsed laser light L1 and monitoring light L2 and the pulsed laser light L1 radiated to the thrombus T. As illustrated in FIG. 3, the bubble TB is normally generated within 10 μs of the radiation of the pulsed laser light L1. The generated bubble TB grows with an elapse of time and then shrinks and disappears. The bubble TB whose volume is increased after being generated has a volume decreased after a peak of the increase and finally disappears. A duration time of the bubble TB (a time from the generation of the bubble TB to the disappearance) is at most about 2 ms. The duration time of the bubble TB depends on various conditions such as an amount of input energy of the pulsed laser light L1.

In the illustrated example, the frequency of the pulsed laser light L1 is 5 Hz. That is, the pulsed laser light L1 having a cycle of 200 ms is radiated from the other end of the optical fiber 7. The pulse width of the pulsed laser light L1 is 100 μs. The bubble TB generated by one pulse of the pulsed laser light L1 disappears before the next pulse is radiated. In this case, reflection or scattering of the pulsed laser light L1 by the bubble TB occurs after 10 μs from the start of the radiation of the pulsed laser light L1 until 0.1 ms, and a part of the reflected or scattered pulsed laser light L1 becomes the returned light L3.

On the other hand, the monitoring light L2 is the continuous wave light. The monitoring light L2 is continuously radiated from the generation of the bubble TB to the disappearance thereof. During a period from the generation of the bubble TB to the disappearance thereof, reflection or scattering of the monitoring light L2 by the bubble TB occurs, and a part of the reflected or scattered monitoring light L2 becomes the returned light L3. In the present embodiment, a reaction in the blood vessel BV is evaluated on the basis of the time waveform of the returned light L3 of the monitoring light L2.

Next, parameters for evaluating the reaction of the blood vessel BV according to radiation of the pulsed laser light L1 will be described.

In the present embodiment, the evaluation in the blood vessel BV can be performed using a parameter related to the waveform area (the integrated value) of the time waveform acquired by the analysis unit 9. Because the returned light L3 is generated when the monitoring light L2 is reflected or scattered by the bubble TB, the returned light L3 is continuously detected during the period from the generation of the bubble TB to the disappearance thereof. Thus, a waveform area from the radiation of the pulsed laser light L1 to a convergence of amplitude (intensity) thereof in the time waveform can be used as the parameter.

Figure 4:
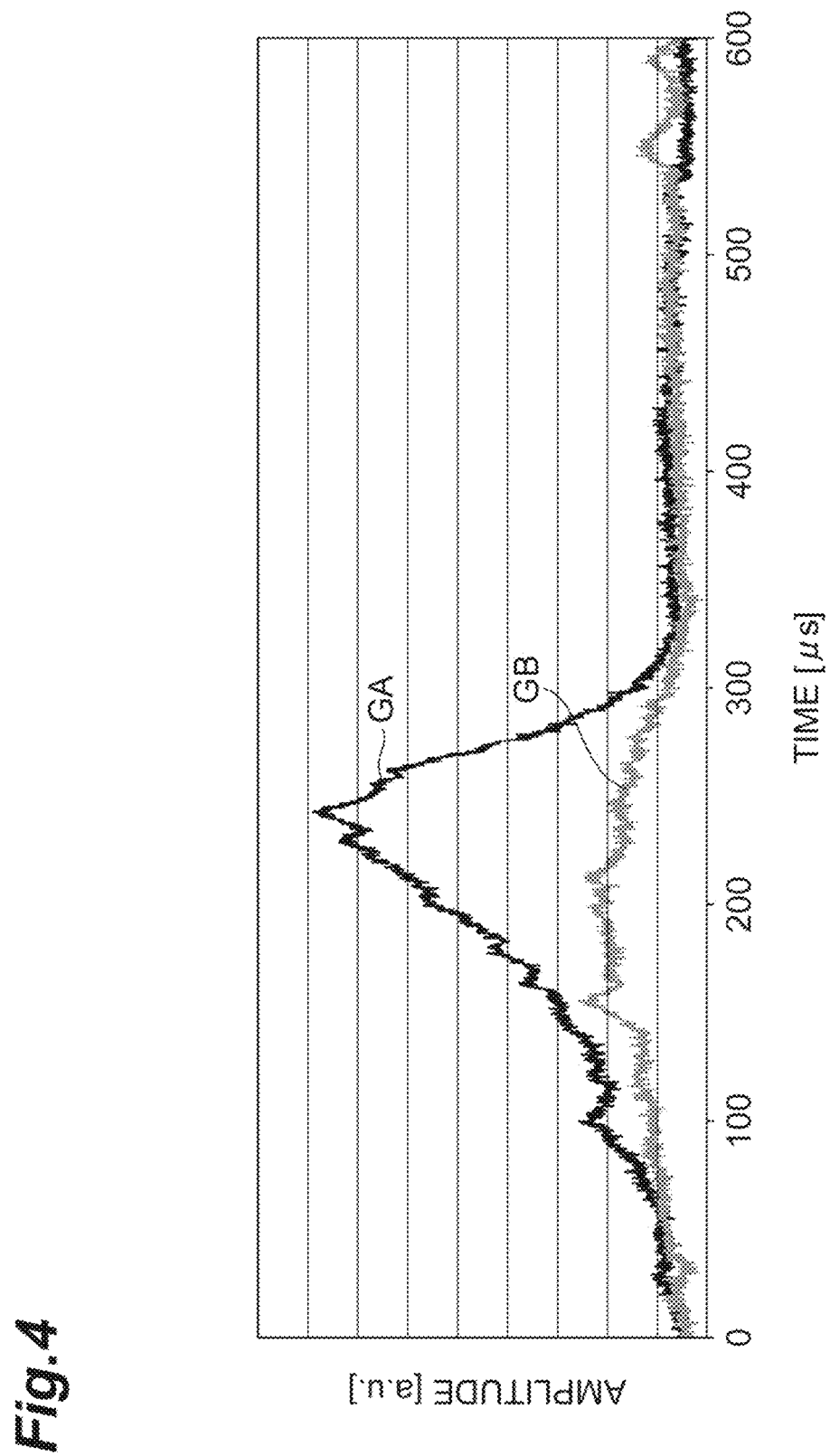
FIG. 4 is a graph illustrating a time waveform measured by the monitoring device.

Also, the convergence time of the time waveform can be used as the parameter. A shape and the like of the bubble TB generated by the radiation of the pulsed laser light L1 depend on various factors such as states of a radiation target. Thus, a state of the returned light L3 reflected or scattered by the bubble TB may also differ according to the radiation of the pulsed laser light L1. For example, FIG. 4 is a graph illustrating a time waveform and illustrates time waveforms GA and GB of the returned light L3 in two pieces of pulsed laser light L1 with the same radiation condition. In FIG. 4, the radiation of the pulsed laser light L1 is started when the time is 0 μs. As illustrated in FIG. 4, even when the radiation condition of the pulsed laser light L1 is the same, there is a difference in an amplitude intensity of the returned light L3 obtained by the photodetector 8. For example, in the time waveform GA, a peak is formed in accordance with growth and shrinkage of the bubble TB. On the other hand, the time waveform GB has no conspicuous peak and has a broad waveform.

Figure 5:
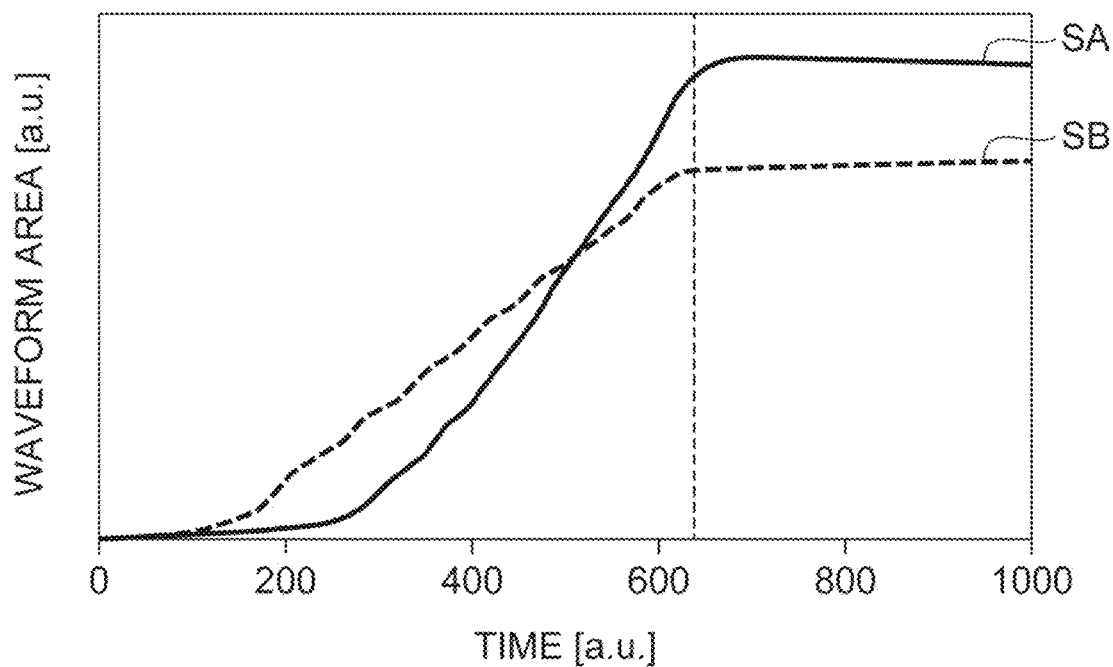
FIG. 5 is a graph illustrating a change in a waveform area over time in the time waveform measured by the monitoring device.

FIG. 5 is a graph schematically illustrating changes in waveform areas in two such types of time waveforms over time. In FIG. 5, the waveform area of the time waveform is plotted on a vertical axis. As illustrated in FIG. 5, in two graphs SA and SB, sizes of converged waveform areas are different. However, a time required for convergence of the waveform areas is substantially the same. This time is considered to be the duration time of the bubble TB.

Figure 6:
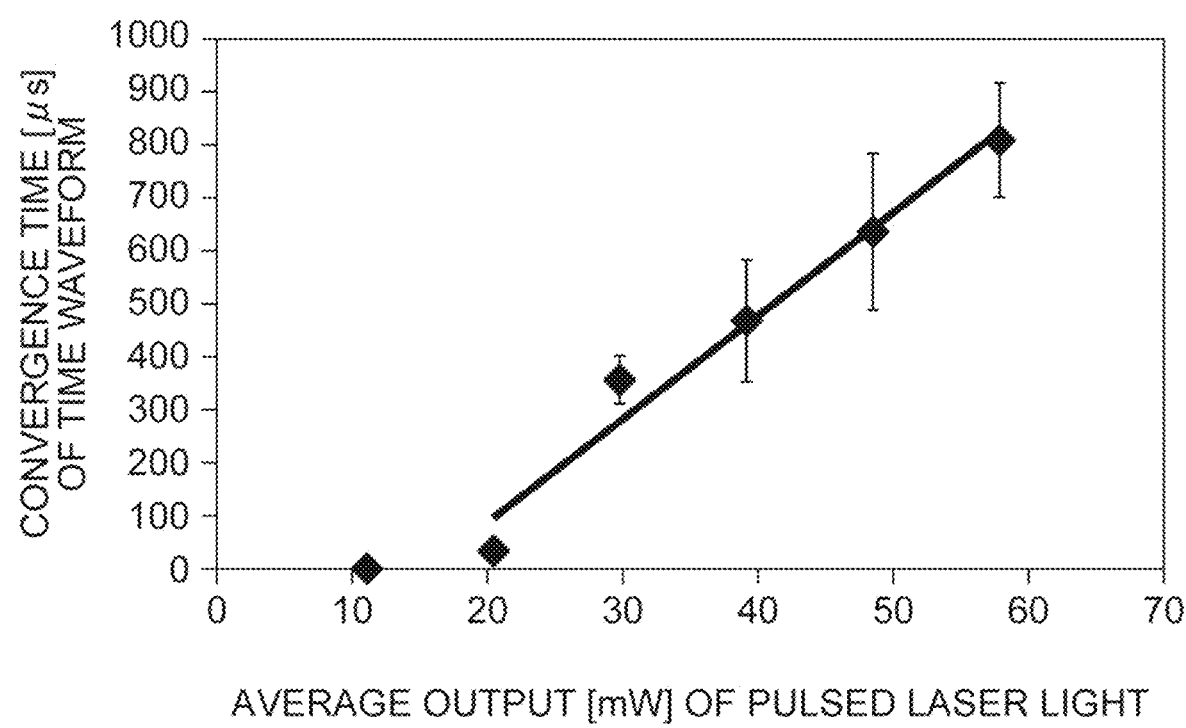
FIG. 6 is a graph illustrating a relationship between an average output of pulsed laser light and a convergence time of the time waveform.
Figure 7:
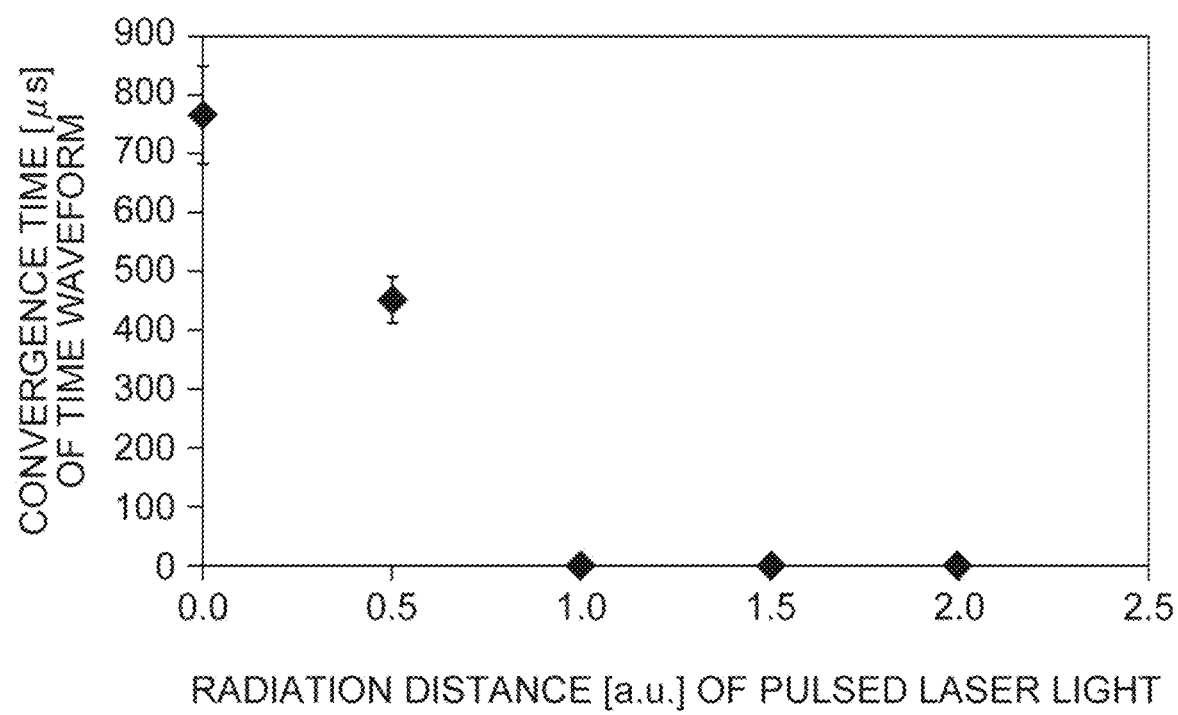
FIG. 7 is a graph illustrating a relationship between a radiation distance of the pulsed laser light and the convergence time of the time waveform.

FIG. 6 is a graph illustrating a relationship between an average output of the radiated pulsed laser light L1 and a convergence time of a time waveform acquired by the analysis unit 9. As illustrated in FIG. 6, if conditions other than the output of the pulsed laser light L1 are set to be the same, the convergence time of the time waveform has a linear relationship with the average output of the pulsed laser light L1. FIG. 7 is a graph illustrating a relationship between a radiation distance and a convergence time of a time waveform when a distance from a distal end of a catheter to a pseudo thrombus (gelatin phantom) is set as a radiation distance of the pulsed laser light L1. As illustrated in FIG. 7, the convergence time of the time waveform increases as the radiation distance of the pulsed laser light L1 decreases. From such a result, it is possible to accurately evaluate a dynamic state of the bubble TB by using the convergence time of the time waveform as the parameter.

In the two graphs illustrated in FIG. 5, sizes of the waveform areas are different, as described above. This is considered to be due to a dynamic state such as a growth rate of the bubble TB. The growth of the bubble TB depends on an amount of input energy of the pulsed laser light L1 as well as a surrounding environment such as hardness of a radiation target. Thus, if different reactions are detected under the same radiation condition, it is possible to evaluate that a target state is different. For example, in the case of a thrombus whose hardness is different from that of a normal thrombus, a size of the waveform area in the time waveform of the returned light L3 is different from a normal size thereof. Also, because thrombus removal can be achieved by the physical action of the bubble TB as described above, stress is also applied to the optical fiber 7 every time the bubble TB is generated. Thus, even in the bubble TB generated under the same radiation condition, a state of reflection or scattering of the monitoring light L2 may be different. Such a difference mainly appears as a difference in the peak intensity of the time waveform. The duration time of the bubble TB converges for each radiation condition. Thus, by detecting the duration time of the time waveform, it is possible to accurately evaluate the dynamic state of the bubble TB. If the peak intensity is also averaged, the averaged peak intensity converges on each condition (see FIG. 8A).

Also, parameters related to a peak time, which is a time when a peak appears in the time waveform, can be used. FIGS. 8A and 8B are graphs illustrating an example of a time waveform measured by the monitoring device 20. In FIGS. 8A and 8B, radiation of the pulsed laser light L1 is started when the time is 0 μs. FIG. 8A illustrates an example of a time waveform when the pulsed laser light L1 with an average output of 36.1 mV is radiated four times under the same radiation condition. Also, FIG. 8B illustrates an example of a time waveform when the pulsed laser light L1 having an average output of 73.4 mV is radiated four times. As illustrated in FIGS. 8A and 8B, in the time waveform of the returned light L3, the maximum value of the amplitude is observed as a peak. For example, in FIG. 8A, the peak appears at a position of about 250 μs on average from the start of the radiation of the pulsed laser light L1. In FIG. 8B, the peak appears at a position of about 400 μs on average from the start of the radiation with the pulsed laser light L1. In FIGS. 8A and 8B, the peak appearing immediately after the start of the radiation with the pulsed laser light L1 is caused by the wavelength component of the pulsed laser light L1 that cannot be attenuated by the band-pass filter 15 in the returned light L3.

Figure 9:
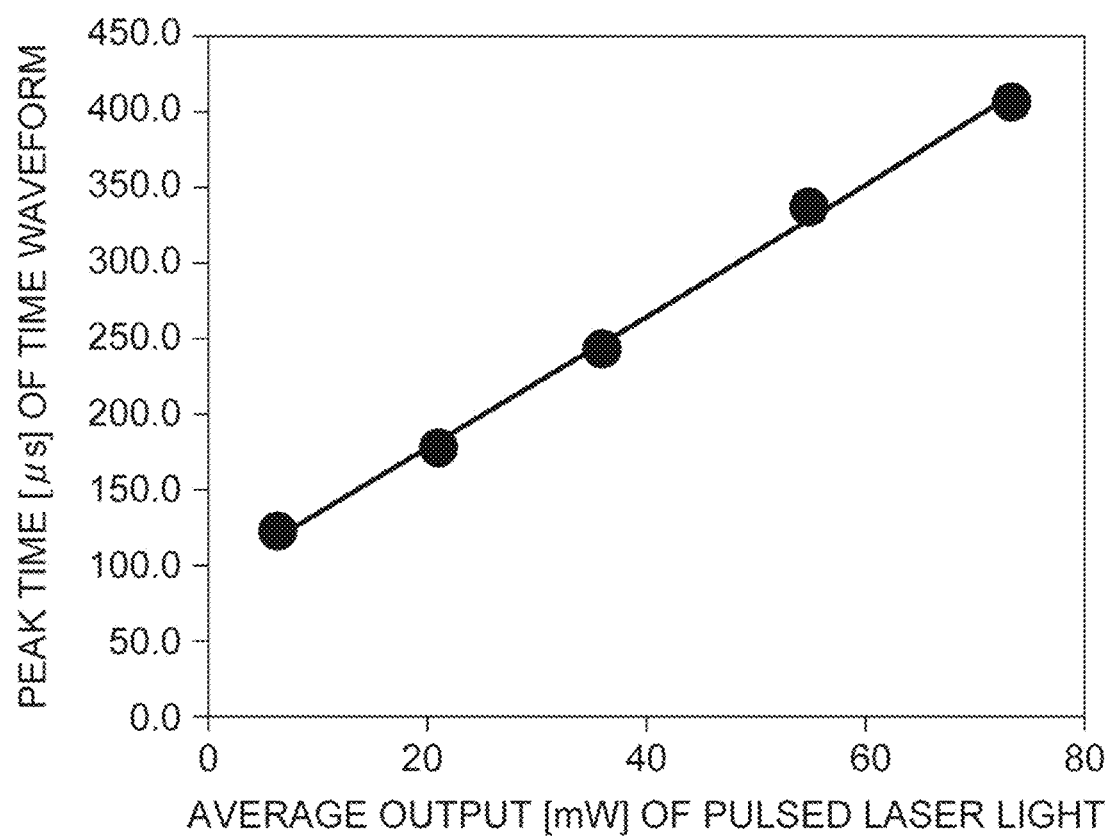
FIG. 9 is a graph illustrating a relationship between an average output of pulsed light radiated by a light radiation device and a peak time of a time waveform measured by the monitoring device.

FIG. 9 is a graph illustrating a relationship between the average output of the pulsed laser light L1 and the peak time of the time waveform measured by the monitoring device 20. As illustrated in FIG. 9, the peak time of the time waveform has a linear relationship with the average output of the pulsed laser light L1. Normally, as the amount of input energy increases, a size of the generated bubble TB increases. In this case, because a time until the bubble TB is maximized is long, a time until a peak of an acquired time waveform is considered to be increased. That is, a time until the peak is reached can be an index of the size of the bubble TB. Therefore, the time until the peak of the amplitude is reached in the time waveform (a rising time) can be used as the parameter. Also, because there is a correlation between the size of the bubble TB and the convergence time of the time waveform, as described above, the time from the amplitude peak to the convergence (a falling time) may be used as the parameter.

If the conditions under which the bubble TB is generated are the same, the peak intensity, which is the intensity (amplitude) of the peak time in the time waveform, can also be used as a sufficiently useful parameter. Also, the waveform pattern in the time waveform may be used as the parameter. For example, a physical property, such as hardness, is different between blood B and the thrombus T. Thus, even when the same pulsed laser light L1 is radiated, a difference in the peak intensity and the waveform pattern may occur. For example, the size of the bubble TB when the pulsed laser light L1 is radiated toward the blood B is larger than in the case of the thrombus T.

The presence or absence of a peak in the time waveform may be used as the parameter. As illustrated in FIG. 7, if the radiation distance of the pulsed laser light L1 is increased, the reaction gradually decreases, and an effect of the radiation of the pulsed laser light L1 eventually cannot be obtained. That is, because no bubble TB is generated if the radiation distance is greater than or equal to a predetermined length, no peak appears in the time waveform of the returned light L3.

Next, an example of a method of operating the monitoring device 20 in the light radiation device 1A will be described with reference to FIGS. 10A to 12B.

If laser thrombus therapy is performed using the light radiation device 1A, the catheter C accommodating the optical fiber 7 is inserted into the blood vessel BV, and a distal end of the catheter C is moved to a position close to the thrombus T. In this state, physiological saline S is injected into the catheter C, and the physiological saline S is administered into the blood vessel BV from the distal end of the catheter C. A position of the catheter C in the blood vessel BV is confirmed, for example, by imaging a metallic marker M attached to the distal end side of the catheter C with an X-ray transmission device. Then, the pulsed laser light L1 is output from the therapeutic laser light source 3, and the pulsed laser light L1 is radiated into the blood vessel BV from the other end of the optical fiber 7. Along with the radiation of the pulsed laser light L1, the monitoring device 20 is operated as follows.

That is, the monitoring light L2 is first output from the monitoring laser light source 5, and the monitoring light L2 is radiated into the blood vessel BV from the other end of the optical fiber 7 (an output process). The returned light L3 of the monitoring light L2 output in the output step is detected by the photodetector 8, and a signal (a detection signal) corresponding to the intensity of the returned light L3 is output (a light detection process). On the basis of the signal output in the light detection process, a time waveform is acquired by the analysis unit 9 as a change in the intensity of the returned light L3 over time, and a reaction in the blood vessel BV is evaluated (an analysis process).

Figure 10A:
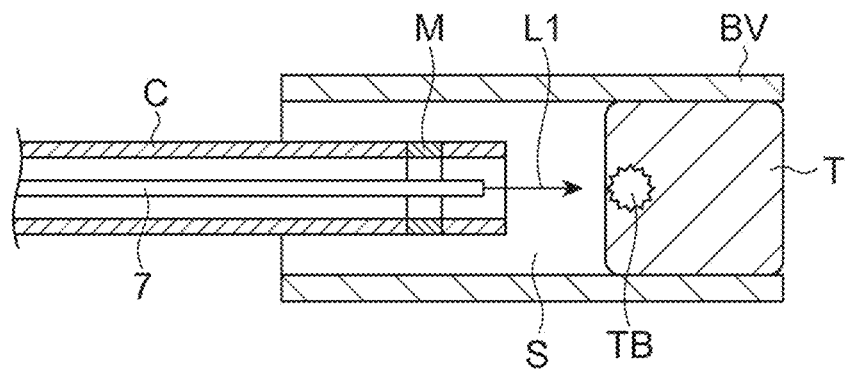
FIG. 10A is a schematic diagram illustrating a state in which a catheter is intubated in a blood vessel.
Figure 10B:
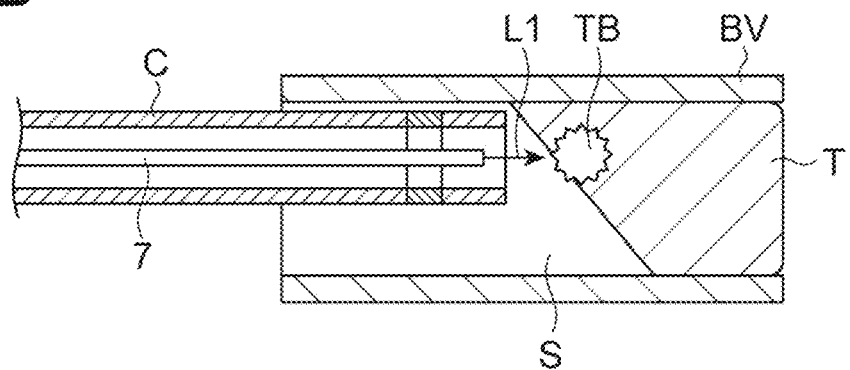
FIG. 10B is a schematic diagram illustrating a state in which the catheter is intubated in a blood vessel.
Figure 10C:
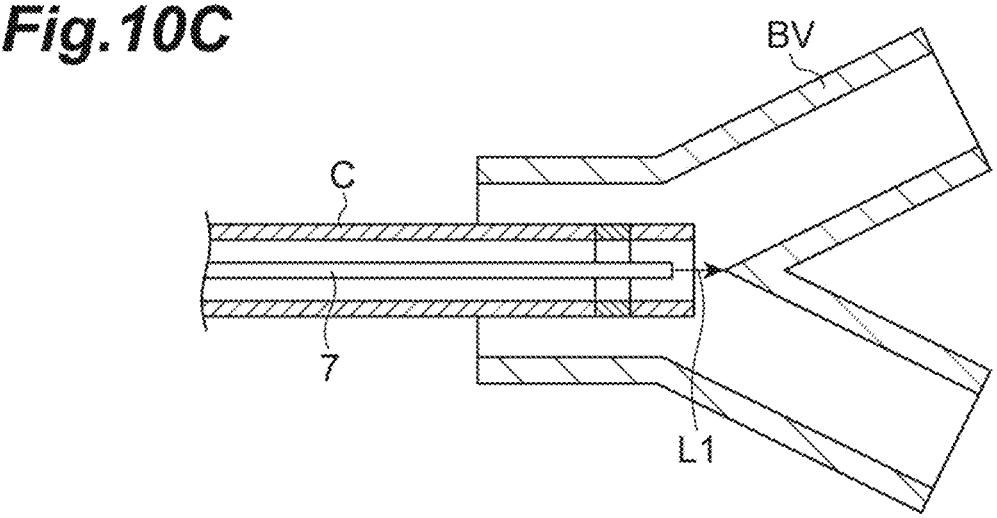
FIG. 10C is a schematic diagram illustrating a state in which the catheter is intubated in a blood vessel.

FIGS. 10A, 10B, and 10C are schematic diagrams illustrating a state in which the catheter C is intubated in the blood vessel By. In the example of FIG. 10A, the position of the distal end of the catheter C is away from the thrombus T. When the pulsed laser light L1 radiated in blood travels 0.1 mm, 90% or more of the pulsed laser light L1 is absorbed by the blood. Thus, if the distal end of the catheter C is not disposed in the immediate vicinity of the thrombus T, the bubble TB due to the radiation of the pulsed laser light L1 is hardly generated, and an effect of the therapy is remarkably deteriorated. In the example of FIG. 10B, the position of the distal end of the catheter C is close to only a part of the thrombus T. As described above, if the distal end of the catheter C is not close to a majority of the thrombus T, there is a possibility that the effect of the therapy may be reduced. Also, in the example of FIG. 10C, the position of the distal end of the catheter C faces a blood vessel wall instead of the thrombus T. In this case, the pulsed laser light L1 is radiated toward the blood vessel wall instead of the thrombus T, and it is impossible to obtain the effect of the therapy.

In the above states illustrated in FIGS. 10A, 10B, and 10C, even if reflection or scattering of the monitoring light L2 does not occur or occurs, it is smaller than in a normal state. Therefore, it is possible to evaluate that a position of a distal end of the catheter C is away from the thrombus T if the waveform area of the time waveform is extremely small, the peak intensity or the like of the time waveform is extremely small, the convergence time of the time waveform is extremely small, the peak waveform cannot be obtained, or the like. Also, the fact that the waveform area of the time waveform is extremely small means that each acquired value is smaller than a predetermined threshold value.

FIGS. 11A, 11B, and 11C are schematic diagrams illustrating a relationship between the state in the blood vessel BV and the time waveform measured by the monitoring device 20. FIG. 11A illustrates an ideal positional relationship between the distal end of the catheter C and the thrombus T. If the distal end of the catheter C is near to the thrombus T, the pulsed laser light L1 is efficiently radiated toward the thrombus T. In this case, the monitoring light L2 is reflected or scattered by the generated bubble 1B and the returned light L3 is increased. Therefore, the position of the distal end of the catheter C can be evaluated to be close to the thrombus T based on the waveform area of the time waveform, the peak intensity of the time waveform, the convergence time of the time waveform, and the like.

FIG. 11B illustrates a state in which therapy has progressed from the state of FIG. 11A. As illustrated in FIG. 11B, when the therapy progresses, a distance from the distal end of the catheter C to the thrombus T increases. In this case, the radiation distance of the pulsed laser light L1 increases, and it is difficult for the bubble TB to be generated. Thereby, the effect of the therapy is deteriorated. The position of the distal end of the catheter C can be evaluated to be away from the thrombus T due to a decrease in the waveform area of the time waveform, a decrease in the peak intensity of the time waveform, a decrease in the convergence time of the time waveform, and the like. As described above, when the position of the catheter C is evaluated to have moved away from the thrombus T, an operation of moving the catheter C to a position close to the thrombus T again is performed, as illustrated in FIG. 11C. Thereby, the bubble 1B is easily generated, and the therapy is efficiently performed. In this case, the returned light L3 increases. That is, the position of the distal end of the catheter C can be evaluated to be close to the thrombus T due to an increase in the waveform area of the time waveform, an increase in the peak intensity of the time waveform, an increase of the convergence time of the time waveform, and the like.

Figure 12A:
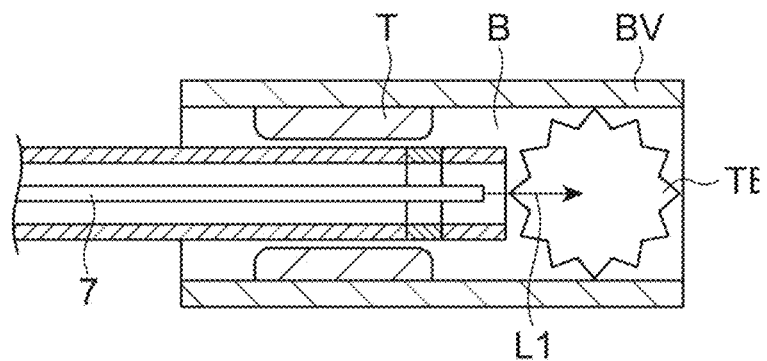
FIG. 12A is a schematic diagram illustrating a state in which the catheter passes through a thrombus.
Figure 12B:
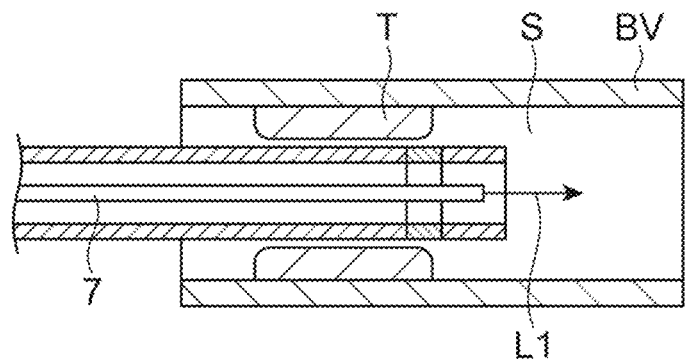
FIG. 12B is a schematic diagram illustrating a state in which the catheter passes through the thrombus.

FIGS. 12A and 12B are schematic diagrams illustrating a state in which the catheter C passes through the thrombus T. By iterating the processes of FIGS. 11A, 11B, and 11C, the distal end of the catheter C passes through the thrombus T. Thereby, the blood vessel BV blocked by the thrombus T is reopened. As a result of securing a flow path, the blood B also flows around the distal end of the catheter C, as illustrated in FIG. 12A. In this case, the radiated pulsed laser light L1 is absorbed by the blood B and the bubble TB is generated. If an amount of input energy of the pulsed laser light L1 is the same, according to in vitro experiment, it can be seen that the bubble TB generated when the pulsed laser light L1 is radiated toward the blood B is larger than the bubble TB generated when the pulsed laser light L1 is radiated toward the thrombus T. Thus, after the reopening of the blood vessel BV, for example, it is possible to observe a change such as an increase in the convergence time in the time waveform of the returned light L3.

However, the physiological saline S is continuously administered into the blood vessel BV from the distal end of the catheter C during the radiation of the pulsed laser light L1. Thus, as illustrated in FIG. 12B, there is a possibility that the blood B is replaced by the physiological saline S. In this case, for example, the convergence time of the time waveform of the returned light L3 may decrease. As described above, in both cases of FIGS. 12A and 12B, different time waveforms are acquired when compared with the case in which the thrombus T is irradiated with the pulsed laser light L1.

An operator can be notified of the evaluation by the monitoring device 20 for the laser thrombus therapy through outputs of a sound, a voice, image display, etc. by the analysis unit 9. Thus, the operator can ascertain the start of therapy, the effect of therapy, the progress of therapy, and the end of therapy in real time.

As described above, according to the present embodiment, the returned light L3 of the monitoring light L2 radiated by the monitoring laser light source 5 is detected by the photodetector 8. The returned light L3 of the monitoring light L2 is generated by the monitoring light L2 being reflected or scattered by the bubble TB generated by the pulsed laser light L1. Here, if the pulsed laser light L1 is appropriately radiated toward the thrombus T and if the pulsed laser light L1 is not appropriately radiated toward the thrombus T, it is found that reactions in the blood vessel BY, such as the presence or absence of the bubble TB and the state until the disappearance of the bubble TB, are different. Then, it is found that the time waveform of the returned light L3 also varies according to such different reactions in the blood vessel BV. Therefore, it is possible to easily evaluate that the pulsed laser light L1 is appropriately radiated toward the thrombus T in the blood vessel BV under an invisible state in real time by evaluating the reaction of the blood vessel BV due to the radiation of the pulsed laser light L1 on the basis of the parameters obtained from the time waveform of the returned light L3. In this case, because the position of the distal end of the catheter C can be ascertained, the radiation of the pulsed laser light L1 toward the blood vessel wall can be minimized. In the above-described embodiment, construction of a new structure at the distal end of the catheter C is unnecessary and a conventionally used catheter can be used as it is.

Examples of the parameters can include a convergence time in a time waveform, a peak time in the time waveform, a peak intensity in the time waveform, a waveform pattern in the time waveform, the presence or absence of a peak in the time waveform, and a waveform area (an integrated value) of the time waveform. According to such parameters, it is possible to appropriately evaluate the reaction in the blood vessel BV due to the radiation of the pulsed laser light L1. These parameters may be used alone or in combination.

Because the monitoring light L2 is continuous wave light, it is possible to facilitate continuous observation from the generation of the bubble TB to the disappearance thereof. Pulsed light may be used as the monitoring light L2, and a reaction in the blood vessel BV may be evaluated on the basis of the returned light L3 of the monitoring light L2. In this case, there is a possibility that it is difficult to perform continuous observation from the generation of the bubble TB to the disappearance thereof according to a relationship between a pulse width of the monitoring light L2 and the duration time of the bubble TB. However, it is possible to evaluate the dynamic state of the bubble TB. If the pulsed light is used as the monitoring light L2, it is possible to perform continuous observation from the generation of the bubble TB to the disappearance thereof by making the pulse width of the monitoring light L2 longer than the duration time of the bubble TB.

The monitoring light L2 has a wavelength in a range of 600 nm to 1300 nm. Because the monitoring light L2 has a wavelength that is unlikely to be absorbed by hemoglobin or moisture, attenuation of the monitoring light L2 can be minimized.

The presence or absence of the bubble TB can be confirmed according to the presence or absence of the returned light L3 itself of the pulsed laser light L1. In this case, for example, it can be confirmed that the thrombus T is located at a position close to the distal end of the optical fiber 7. If no bubble TB occurs, it can be evaluated that the pulsed laser light L1 is not radiated toward the thrombus T. It is conceivable that this case is, for example, because the distal end of the optical fiber 7 is separated from the thrombus T or because the pulsed laser light L1 is radiated toward the blood vessel wall.

Second Embodiment

A light radiation device 1B according to the present embodiment is different from the light radiation device 1A of the first embodiment in that pulsed laser light L1 radiated by a therapeutic laser light source 3 is also used as monitoring light L2. Hereinafter, differences from the first embodiment will be mainly described, the same elements and members will be denoted by the same reference signs, and detailed descriptions thereof will be omitted.

Figure 13:
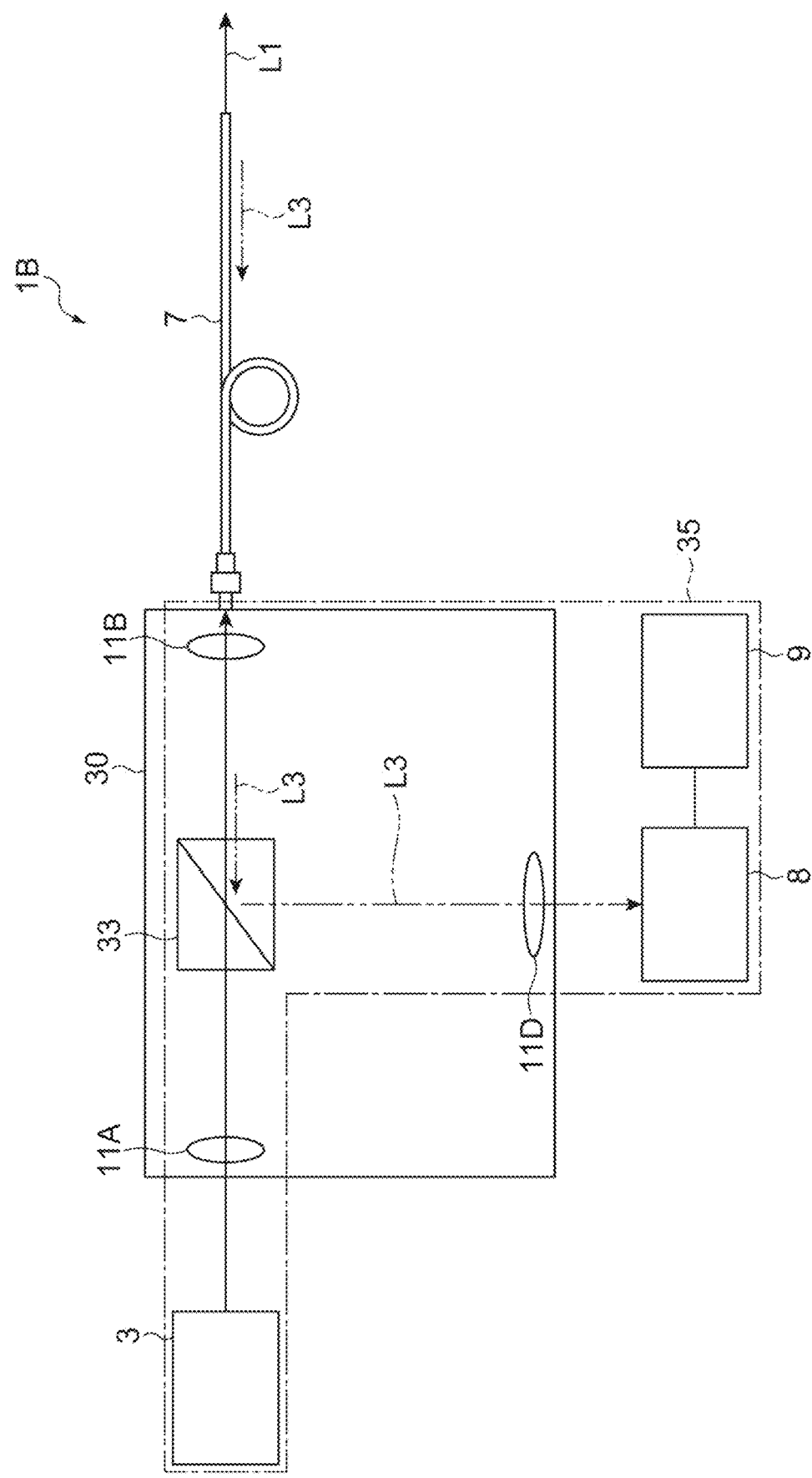
FIG. 13 is a schematic diagram illustrating a light radiation device to which a monitoring device according to another embodiment is applied.

As illustrated in FIG. 13, the light radiation device 1B includes the therapeutic laser light source 3 (a light source or a light output unit), an optical fiber 7, a coupling optical system 30, a photodetector 8, and an analysis unit 9. The coupling optical system 30 optically connects the therapeutic laser light source 3 and one end of the optical fiber 7. The coupling optical system 30 inputs the pulsed laser light L1 output from the therapeutic laser light source 3 to an end surface 7a of the optical fiber 7. The coupling optical system 30 optically connects the one end of the optical fiber 7 and the photodetector 8. The coupling optical system 30 inputs returned light L3 from the optical fiber 7 to the photodetector 8. The coupling optical system 30 includes three lenses 11A, 11B, and 11D and one beam splitter 33. In the present embodiment, a monitoring device 35 is constituted of the therapeutic laser light source 3, the photodetector 8, the analysis unit 9, and a part of the coupling optical system 30. The lenses 11A, 11B, and 11D and the beam splitter 33 of the coupling optical system 30 belong to the monitoring device 35.

The beam splitter 33 is disposed between the lens 11A and the lens 11B on the optical path of the pulsed laser light L1 output from the therapeutic laser light source 3. The beam splitter 33 is constituted of, for example, a half mirror. The lens 11D is disposed between the beam splitter 33 and the photodetector 8 on an optical path of the returned light L3.

The pulsed laser light L1 output from the therapeutic laser light source 3 becomes parallel light via the lens 11A and is input to the one end surface 7a of the optical fiber 7 through the lens 11B. The pulsed laser light L1 input to the one end surface 7a of the optical fiber 7 is output from the other end surface 7b of the optical fiber 7. The returned light L3 from the optical fiber 7 becomes parallel light via the lens 11B and is input to the beam splitter 33. The beam splitter 33 outputs the input returned light L3 toward the photodetector 8. The returned light L3 is input to the photodetector 8 via the lens 11D.

When a bubble TB is generated by radiation of the pulsed laser light L1, reflection or scattering of the pulsed laser light L1 by the bubble TB occurs, and a part of the pulsed laser light L1 becomes the returned light L3. That is, in the present embodiment, the pulsed laser light L1 also functions as monitoring light. The analysis unit 9 analyzes the returned light L3 of the pulsed laser light L1 so that it is possible to evaluate a dynamic state of the bubble TB.

Also in the present embodiment, the same action and effect as in the first embodiment are exerted. In particular, in the present embodiment, the monitoring light radiated into a blood vessel BV in order to evaluate a reaction in the blood vessel BV is the pulsed laser light L1. Because the pulsed laser light L1 also serves as the monitoring light, it is possible to eliminate the need for a separate light source such as the monitoring laser light source 5 (see FIG. 1). In this case, there is a possibility that it is difficult to perform continuous observation from the generation of the bubble TB to a disappearance thereof according to a relationship between a pulse width of the pulsed laser light L1 and a duration time of the bubble TB. However, even in this case, it is possible to evaluate the dynamic state of the bubble TB.

Although the embodiments have been described with reference to the drawings, specific configurations are not limited to the embodiments.

Figure 14A:
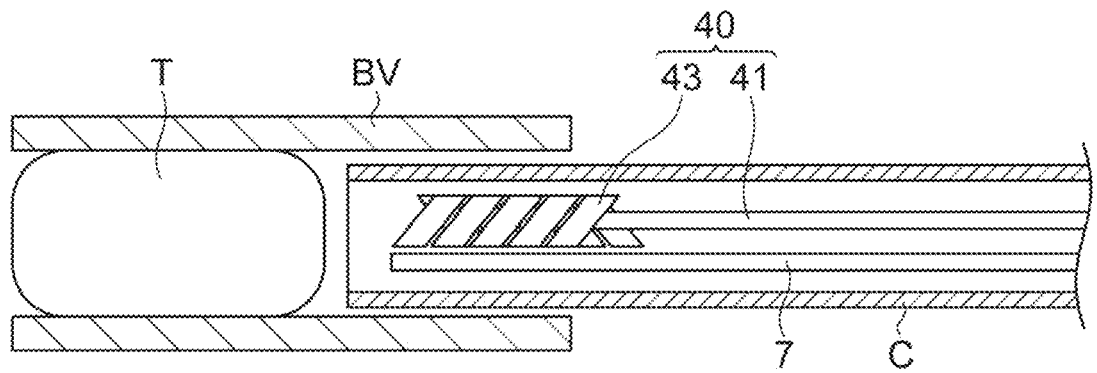
FIG. 14A is a schematic diagram illustrating a modified example of a light radiation device to which a monitoring device is applied.
Figure 14B:
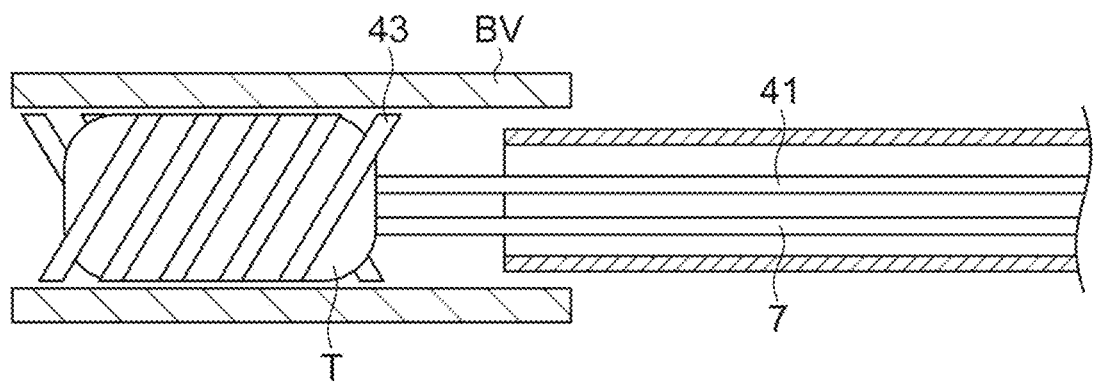
FIG. 14B is a schematic diagram illustrating the modified example of the light radiation device to which the monitoring device is applied.

For example, although an example in which the monitoring devices 20 and 35 are applied to the light radiation devices 1A and 1B for laser thrombus therapy has been described in each of the above-described embodiments, the present disclosure is not limited thereto. For example, the monitoring devices 20 and 35 may be applied to a mechanical therapeutic device. FIGS. 14A and 14B are schematic diagrams illustrating therapy of a thrombus T with a mechanical therapeutic device. As illustrated in FIGS. 14A and 14B, the mechanical therapeutic device includes a catheter C, an optical fiber 7 accommodated in the catheter C, and a thrombus catcher 40 accommodated in the catheter C. The thrombus catcher 40 includes, for example, a wire 41 and a helical catcher 43 provided at a distal end of the wire 41. In such a mechanical therapeutic device, the catheter C is disposed in the immediate vicinity of the thrombus T, and the thrombus T can be removed by the catcher 43 of the thrombus catcher 40. In this case, a position of the catheter C can be easily confirmed in real time by monitoring returned light L3 of at least one of pulsed laser light L1 and monitoring light L2 radiated from the optical fiber 7. In an operation of pulling out the thrombus T, it is possible to confirm whether or not the thrombus T has fallen off the catcher 43.

Figure 15:
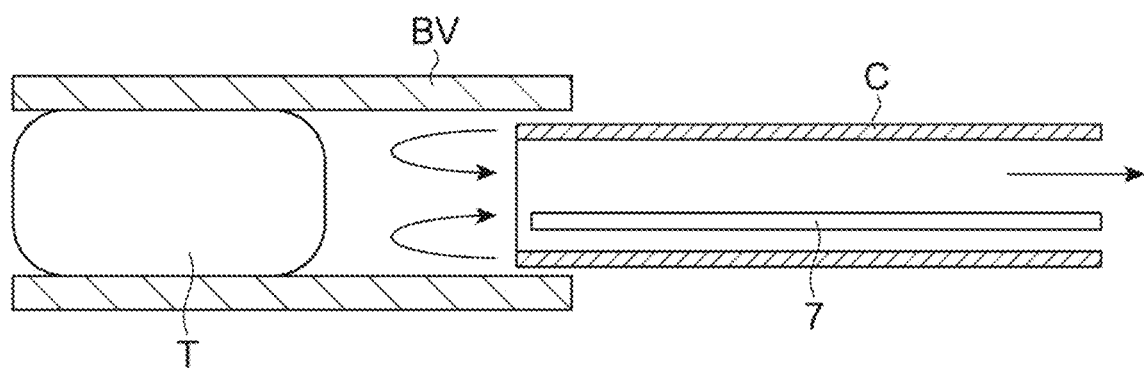
FIG. 15 is a schematic diagram illustrating another modified example of the light radiation device to which the monitoring device is applied.

For example, the monitoring devices 20 and 35 may be applied to other mechanical therapeutic devices. FIG. 15 is a schematic diagram illustrating therapy of a thrombus T by another mechanical therapeutic device. As illustrated in FIG. 15, the mechanical therapeutic device includes a catheter C and an optical fiber 7 accommodated in the catheter C. In this mechanical therapeutic device, the catheter C can be disposed in the immediate vicinity of the thrombus T, and the thrombus T can be suctioned by the catheter C. In this case, position confirmation of the catheter C can be easily performed in real time by monitoring returned light L3 of at least one piece of pulsed laser light L1 and monitoring light L2 radiated from the optical fiber 7. Also, it is possible to confirm whether or not the thrombus T is reliably suctioned without suctioning a blood vessel wall or the like.

Figure 16:
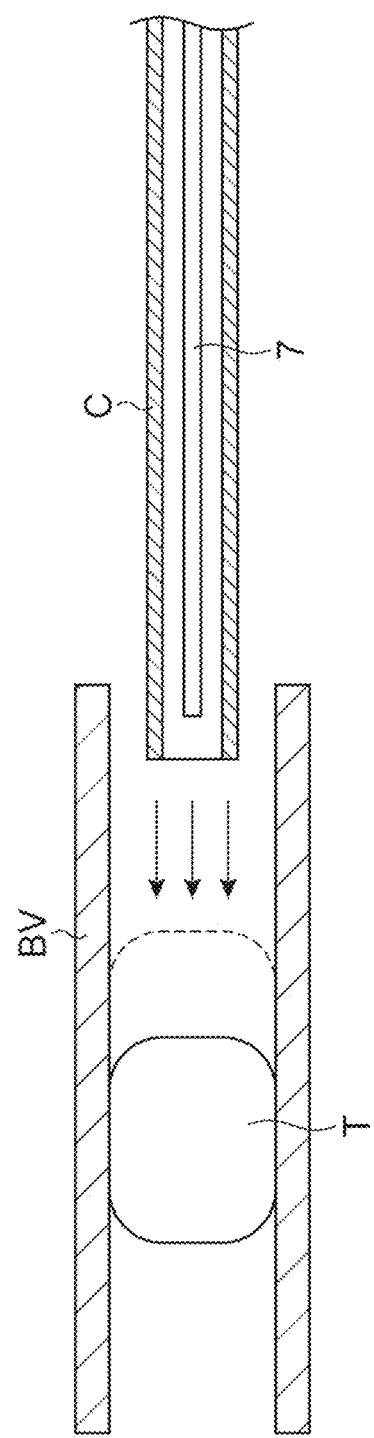
FIG. 16 is a schematic diagram illustrating still another modified example of the light radiation device to which the monitoring device is applied.

For example, the monitoring devices 20 and 35 may be applied to a medication administration device. FIG. 16 is a schematic diagram illustrating therapy of a thrombus T by the medication administration device. As illustrated in FIG. 16, the medication administration device includes a catheter C and an optical fiber 7 accommodated in the catheter C. In this medication administration device, the catheter C can be disposed in the immediate vicinity of the thrombus T, and a medication can be administered from a distal end of the catheter C to the thrombus T. In this case, it is possible to easily confirm a position of the catheter C in real time by monitoring pulsed laser light L1 emitted from the optical fiber 7 or returned light L3 of monitoring light L2. Also, it is possible to confirm whether or not an effect of thrombolysis is obtained by the administration of the medication. Also, it is possible to confirm the presence or absence of the thrombus T.

Although the beam splitter is used for the coupling optical systems 10 and 30 in each of the above-described embodiments, optical parts including light coupling and light separation functions such as an optical fiber coupler and an optical fiber combiner may also be used instead of the beam splitter.

According to the monitoring device and the method of operating the monitoring device according to one aspect, it is possible to easily evaluate that pulsed light is appropriately radiated into a blood vessel.

What is claimed is:

1. A device for radiating pulsed light toward a thrombus in a blood vessel, the device comprising:
a first light source configured to output the pulsed light to be radiated toward the thrombus in the blood vessel;
a second light source configured to output monitoring light to be radiated into the blood vessel;
a light detector configured to detect returned light of the monitoring light and output a detection signal, the returned light of the monitoring light being reflected and/or scattered by a bubble generated in the blood vessel by the pulsed light radiated toward the thrombus; and
a computer configured to acquire a time waveform, which is a change in an intensity of the returned light over time, based on the detection signal,
wherein the computer is configured to obtain a parameter on the basis of the time waveform and evaluates a reaction in the blood vessel according to the radiation of the pulsed light on the basis of the parameter, and
wherein the parameter is a waveform area of the time waveform.

2. The device according to claim 1, wherein the parameter further includes at least one of a convergence Lime in the time waveform, a peak time in the time waveform, a peak intensity in the time waveform, a waveform pattern in the time waveform, and presence or absence of a peak in the time waveform.

3. The device according to claim 1, wherein the monitoring light is continuous wave light.

4. The device according to claim 2, wherein the monitoring light is continuous wave light.

5. The device according to claim 1, wherein the monitoring light has a wavelength in a range of 600 nm to 1300 nm.

6. The device according to claim 2, wherein the monitoring light has a wavelength in a range of 600 nm to 1300 nm.

7. The device according to claim 3, wherein the monitoring light has a wavelength in a range of 600 nm to 1300 nm.

8. The device according to claim 4, wherein the monitoring light has a wavelength in a range of 600 nm to 1300 nm.

9. A method for radiating pulsed light toward a thrombus in a blood vessel, the method comprising:
radiating the pulsed light toward the thrombus in the blood vessel;
radiating monitoring light into the blood vessel;
detecting returned light of the monitoring light by a light detector and outputting a detection signal, the returned light of the monitoring light being reflected and/or scattered by a bubble generated in the blood vessel by radiating the pulsed light toward the thrombus;
acquiring a time waveform, which is a change in an intensity of the returned light over time, based on the detection signal;
obtaining a parameter based on the time waveform; and
evaluating a reaction in the blood vessel according to the radiation of the pulsed light based on the parameter,
wherein the parameter is a waveform area of the time waveform.

10. The method according to claim 9, wherein the parameter further includes at least one of a convergence time in the time waveform, a peak time in the time waveform, a peak intensity in the time waveform, a waveform pattern in the time waveform, and presence or absence of a peak in the time waveform.

11. The method according to claim 9, wherein the monitoring light is continuous wave light.

12. The method according to claim 10, wherein the monitoring light is continuous wave light.

13. The method according to claim 9, wherein the monitoring light has a wavelength in a range of 600 nm to 1300 nm.

14. The method according to claim 10, wherein the monitoring light has a wavelength in a range of 600 nm to 1300 nm.

15. The method according to claim 11, wherein the monitoring light has a wavelength in a range of 600 nm to 1300 nm.

16. The method according to claim 12, wherein the monitoring light has a wavelength in a range of 600 nm to 1300 nm.

* * * * *